(12) United States Patent
Ito et al.

(10) Patent No.: US 10,281,404 B2
(45) Date of Patent: May 7, 2019

(54) SURFACE-ENHANCED RAMAN SCATTERING UNIT AND RAMAN SPECTROSCOPIC ANALYSIS METHOD

(71) Applicant: HAMAMATSU PHOTONICS K.K., Hamamatsu-shi, Shizuoka (JP)

(72) Inventors: Masashi Ito, Hamamatsu (JP); Katsumi Shibayama, Hamamatsu (JP); Kazuto Ofuji, Hamamatsu (JP); Hiroki Oyama, Hamamatsu (JP); Yoshihiro Maruyama, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/928,886

(22) Filed: Mar. 22, 2018

(65) Prior Publication Data

US 2018/0224377 A1    Aug. 9, 2018

Related U.S. Application Data

(63) Continuation of application No. 14/780,728, filed as application No. PCT/JP2014/052926 on Feb. 7, 2014, now Pat. No. 9,952,158.

(30) Foreign Application Priority Data

Mar. 29, 2013   (JP) .................... 2013-073308

(51) Int. Cl.
*G01N 21/53* (2006.01)
*G01N 21/65* (2006.01)

(52) U.S. Cl.
CPC ................... *G01N 21/658* (2013.01)

(58) Field of Classification Search
CPC ........ G01N 21/658; G01N 30/02; G01N 1/40; G01N 2035/1053; G01N 30/6004;
(Continued)

(56) References Cited

U.S. PATENT DOCUMENTS 6,614,523 B1   9/2003   Boss et al.
7,483,130 B2   1/2009   Baumberg et al.
(Continued)

FOREIGN PATENT DOCUMENTS

CN   101281133   10/2008
CN   101319994   12/2008
(Continued)

OTHER PUBLICATIONS

U.S. Office Action dated Jun. 9, 2017 that issued in U.S. Appl. No. 14/780,776 including Double Patenting Rejections on pp. 8-11.
(Continued)

*Primary Examiner* — Michael P Stafira
(74) *Attorney, Agent, or Firm* — Drinker Biddle & Reath LLP

(57) ABSTRACT

A SERS unit 1A comprises a SERS element 2 having a substrate and an optical function part 20 formed on the substrate, the optical function part 20 for generating surface-enhanced Raman scattering; a measurement board 3 supporting the SERS element 2 upon measurement; and a holding part 4 mechanically holding the SERS element 2 in the measurement board 3.

10 Claims, 23 Drawing Sheets

(58) Field of Classification Search
CPC .... G01N 2030/009; G01N 1/405; G01N 1/34;
G01N 2030/525; G01N 21/554; G01N
2030/062; G01N 2035/103; G01N 21/03;
G01N 35/10
See application file for complete search history.

(56) References Cited

U.S. PATENT DOCUMENTS

| | | | |
|---|---|---|---|
| 7,864,313 B2 | 1/2011 | Baumberg et al. | |
| 2003/0059820 A1* | 3/2003 | Vo-Dinh | B01J 19/0046 506/3 |
| 2003/0235520 A1 | 12/2003 | Shea et al. | |
| 2004/0023046 A1 | 2/2004 | Schlottig et al. | |
| 2007/0145249 A1* | 6/2007 | Kiesel | G01N 21/05 250/221 |
| 2008/0094621 A1 | 4/2008 | Li et al. | |
| 2008/0218761 A1 | 9/2008 | Nishikawa et al. | |
| 2010/0240144 A1* | 9/2010 | Gilbert | G01N 21/658 436/169 |
| 2010/0296086 A1* | 11/2010 | Wang | G01N 21/658 356/301 |
| 2011/0096157 A1* | 4/2011 | Fine | G02B 21/0008 348/79 |
| 2011/0116089 A1 | 5/2011 | Schmidt et al. | |
| 2011/0166045 A1 | 7/2011 | Dhawan et al. | |
| 2012/0182548 A1* | 7/2012 | Harb | G01N 21/05 356/246 |
| 2013/0252275 A1 | 9/2013 | Tokonami et al. | |
| 2014/0043605 A1 | 2/2014 | Tseng et al. | |

FOREIGN PATENT DOCUMENTS

| | | |
|---|---|---|
| CN | 102282094 | 12/2011 |
| CN | 102483354 | 5/2012 |
| CN | 102713720 | 10/2012 |
| EP | 1 374 989 | 1/2004 |
| EP | 2 352 010 | 8/2004 |
| JP | H07-260646 A | 10/1995 |
| JP | 2009-222507 A | 10/2007 |
| JP | 2007-538264 A | 12/2007 |
| JP | 2008-519254 | 6/2008 |
| JP | 2008-196992 | 8/2008 |
| JP | 2008-268059 A | 11/2008 |
| JP | 2009-047623 A | 3/2009 |
| JP | 2009-103643 A | 5/2009 |
| JP | 2009-236830 | 10/2009 |
| JP | 2011-021085 | 2/2011 |
| JP | 2011-033518 A | 2/2011 |
| JP | 2011-075348 A | 4/2011 |
| JP | 2011-107032 A | 6/2011 |
| JP | 2012-233707 A | 11/2012 |
| JP | 2013-173444 | 9/2013 |
| JP | 2014-196981 | 10/2014 |
| JP | 5779963 | 9/2015 |
| TW | 200728706 | 8/2007 |
| TW | 200932913 | 8/2009 |
| TW | 20111771 | 4/2011 |
| WO | WO 2007/149120 A2 | 12/2007 |
| WO | WO 2012/024006 A2 | 2/2012 |
| WO | WO 2012/077756 | 6/2012 |
| WO | WO 2013/015810 | 1/2013 |
| WO | WO 2014/025033 | 2/2014 |
| WO | WO 2014-025034 A1 | 2/2014 |

OTHER PUBLICATIONS

U.S. Office Action dated Oct. 14, 2016 that issued in U.S. Patent Application No. 14/20,510 including Double Patenting Rejections on pp. 2-14.
English Machine Translation of JP 2011-107032, Nishikawa et al., Jun. 2, 2011 as attached to U.S. Office Action dated Oct. 14, 2016 in U.S. Appl. No. 14/420,510.
W. Zhang et al., "Giant and uniform fluorescence enhancement over large areas using plamonic nanodots in 3D resonant cavity nanoantenna by nanoimprinting", Nanotechnology, vol. 23, No. 22, May 10, 2012, p. 225301, XP020224099.
S. M. Wells et al., "Efficient disc on pillar substrates for surface enhanced Raman spectroscopy", Chemical Communications—Chemcom, vol. 47, No. 13, Jan. 1, 2011, p. 3814-p. 3816, XP055289549.
K. Nakamoto et al., "Arrays of Metallic Nanopillars in Holes for Plasmonic Devices", Retrieved from the Internet: URL: http://www.rsc.org/images/LOC/2011/PDFs/Papers/596_0021.pdf, Oct. 6, 2011, XP055289892.
M. Tomohiko et al., "New localized surface plasmon resonance sensor utilizing nanoimprinting technology", NSTI Nanotechnology Conference and Trade Show—NSTI Nanotech, vol. 1, May 11, 2006, p. 58-p. 61, XP009098538.
W. D. Li et al., "Three-dimensional cavity nanoantenna coupled plasmonic nanodots for ultrahigh and uniform surface-enhanced Raman scattering over large area", Optics Express, vol. 19, No. 5, Feb. 14, 2011, p. 3925-p. 3936, XP002751299.
Online, Internet, "Q-SERSTM G1 Substrate, URL:http://www.optoscience.com/maker/nanova/pdf/Q-SERS_G1.pdf," Opto Science, Inc., retrieved on Mar. 21, 2013.

* cited by examiner

50nm

Fig.9
(a)
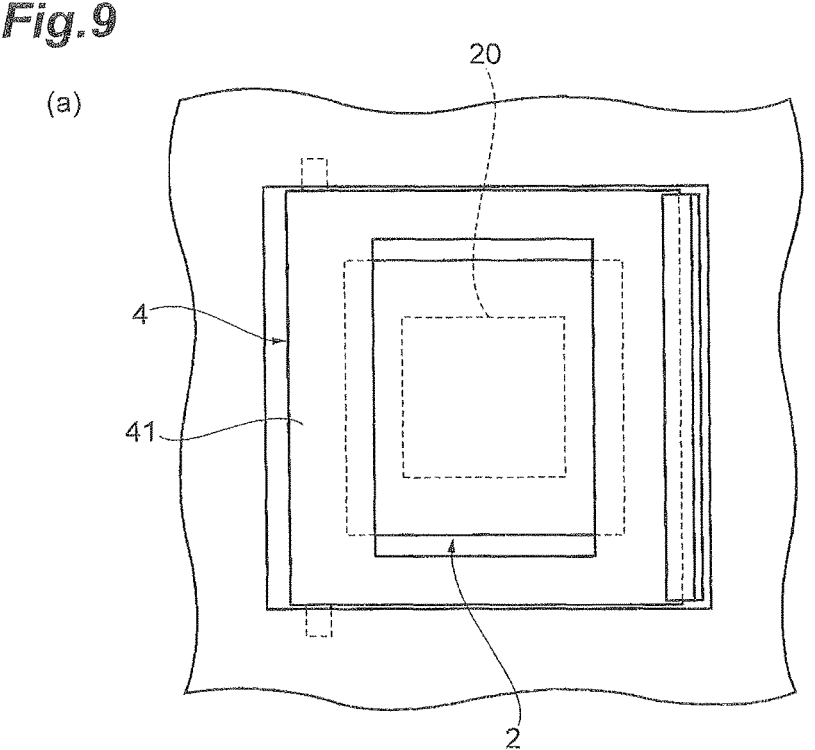
(b)
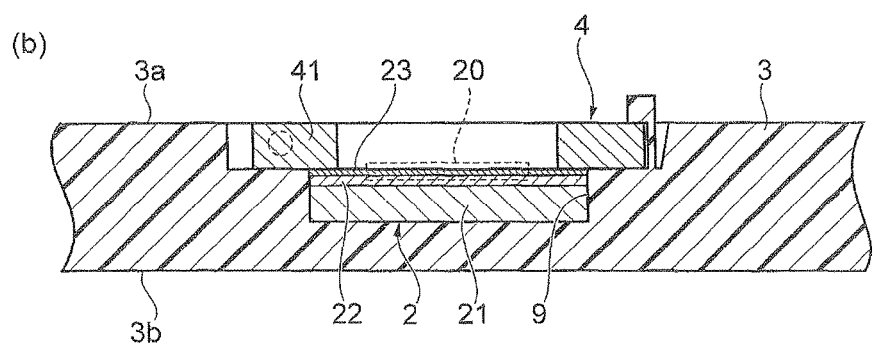

*Fig.13*
(a)
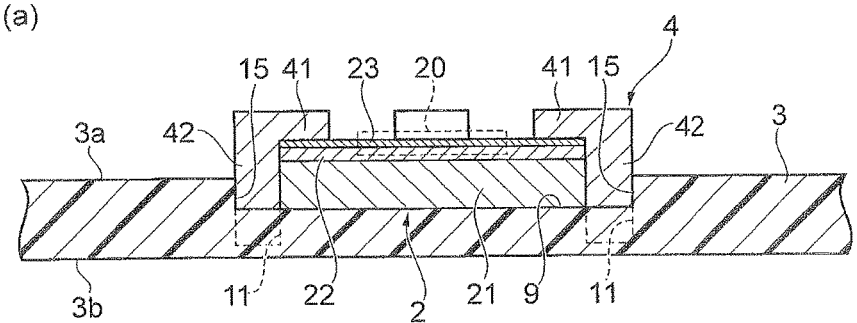
(b)
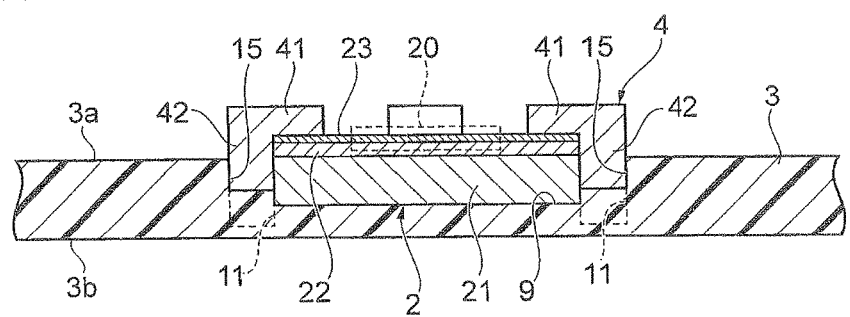

Fig.15
(a)
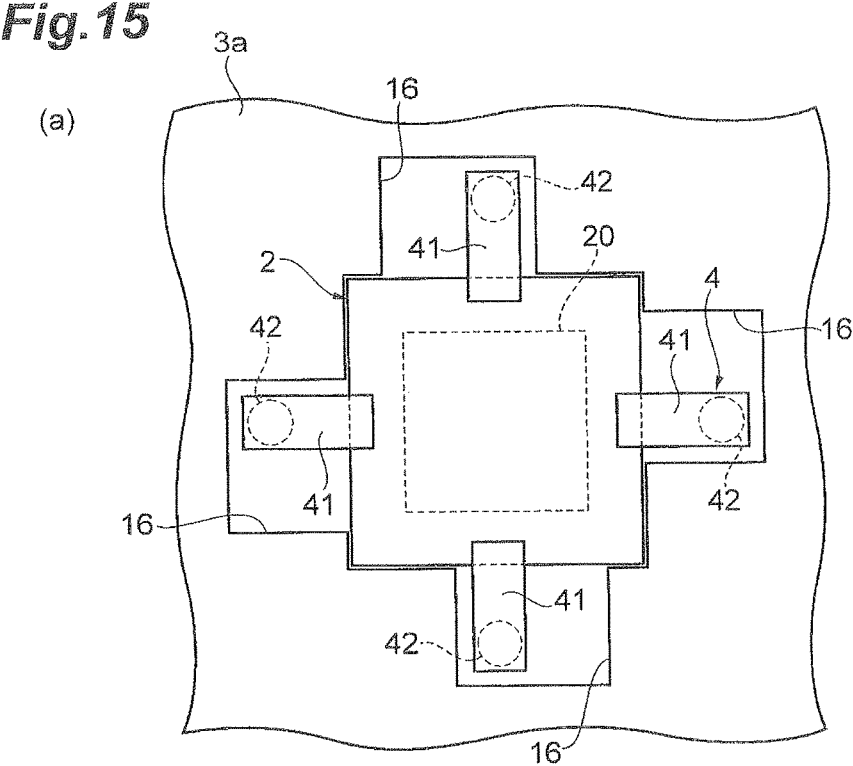
(b)
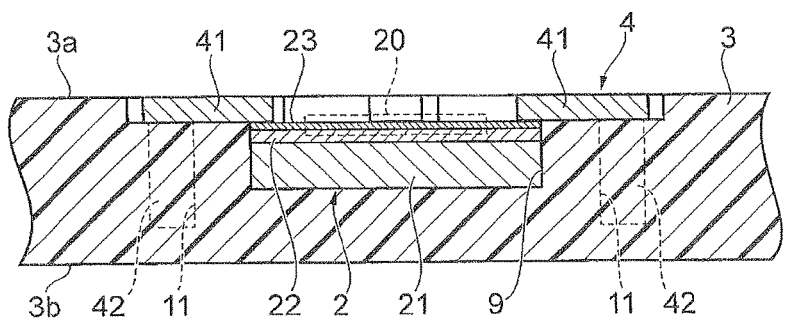

Fig.16
(a)
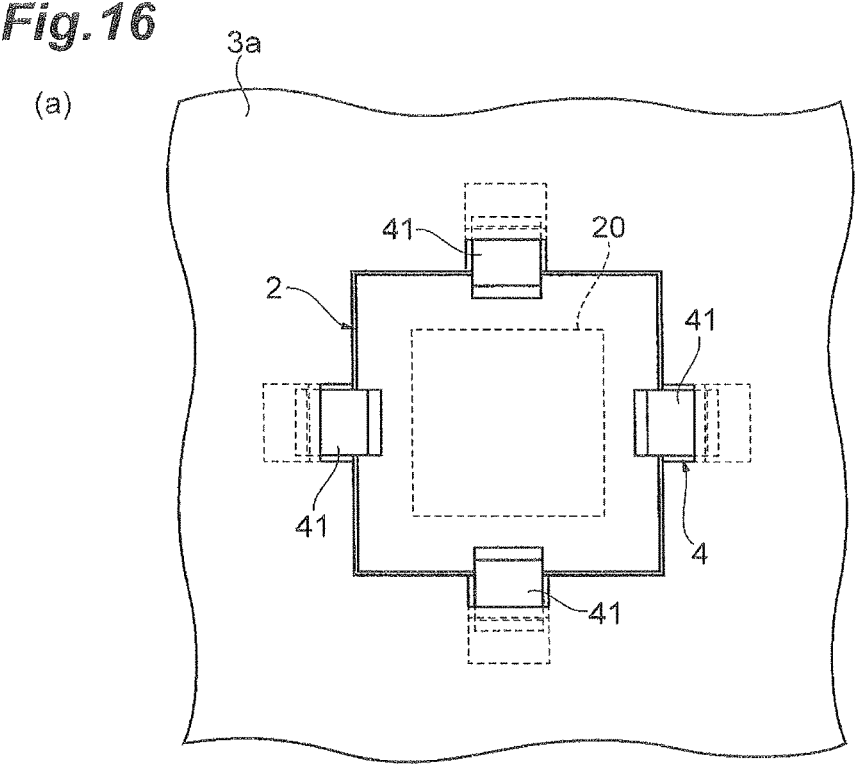
(b)
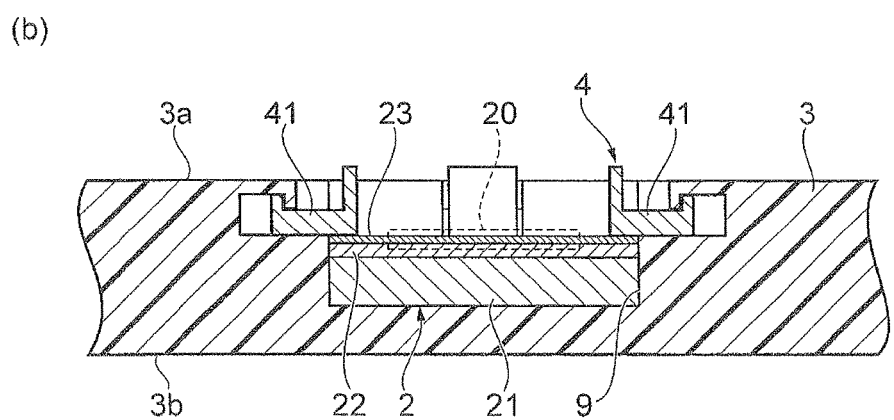

*Fig.18*
(a)
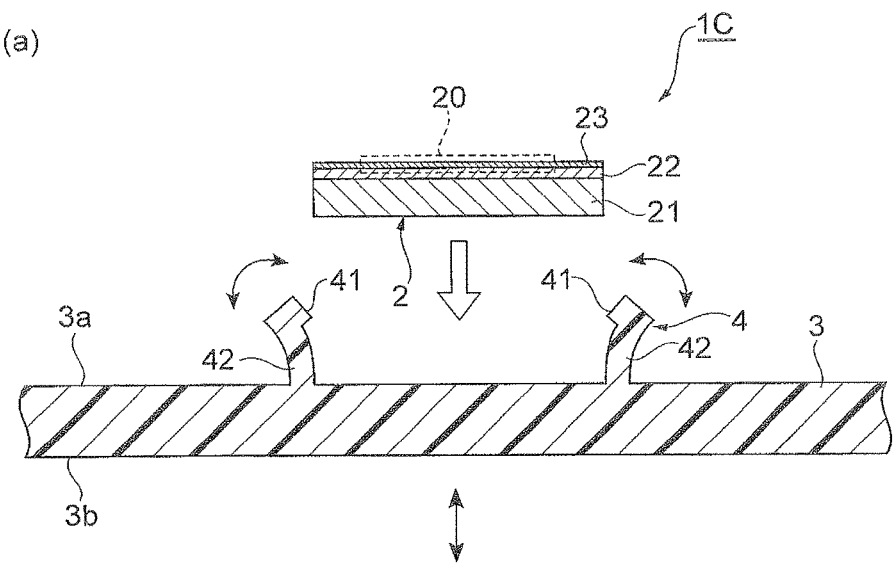
(b)
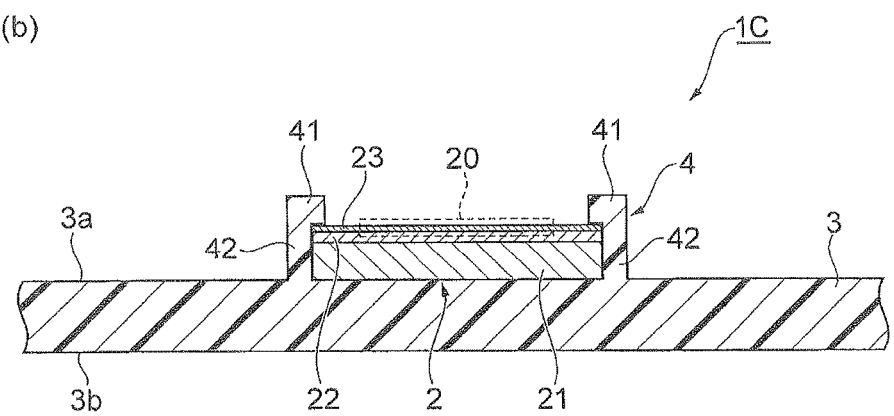

SURFACE-ENHANCED RAMAN SCATTERING UNIT AND RAMAN SPECTROSCOPIC ANALYSIS METHOD

TECHNICAL FIELD

The present invention relates to a surface-enhanced Raman scattering unit and a Raman spectroscopic analysis method.

BACKGROUND ART

Known as a conventional surface-enhanced Raman scattering unit is one in which a surface-enhanced Raman scattering element having an optical function part for generating surface-enhanced Raman scattering (SERS) is secured onto a glass slide (see, for example, Non Patent Literature 1).

CITATION LIST

Non Patent Literature

Non Patent Literature 1: "Q-SERS™ G1 Substrate", [online], Opto Science, Inc., [retrieved on Mar. 21, 2013]. Retrieved from the Internet: <URL: http://www.optoscience.com/maker/nanova/pdf/Q-SERS_G1.pdf>.

SUMMARY OF INVENTION

Technical Problem

In a surface-enhanced Raman scattering unit such as the one mentioned above, the surface-enhanced Raman scattering element is secured onto the glass slide with an adhesive, whereby the optical function part may deteriorate because of ingredients contained in the adhesive.

It is therefore an object of the present invention to provide a surface-enhanced Raman scattering unit which can inhibit the optical function part from deteriorating and a Raman spectroscopic analysis method using such a surface-enhanced Raman scattering unit.

Solution to Problem

The surface-enhanced Raman scattering unit in accordance with one aspect of the present invention comprises a surface-enhanced Raman scattering element having a substrate and an optical function part formed on the substrate, the optical function part for generating surface-enhanced Raman scattering; a measurement board supporting the surface-enhanced Raman scattering element upon measurement; and a holding part mechanically holding the surface-enhanced Raman scattering element in the measurement board.

In this surface-enhanced Raman scattering unit, the holding part mechanically holds the surface-enhanced Raman scattering element in the measurement board. If the surface-enhanced Raman scattering element is secured to the measurement board with an adhesive, for example, deterioration will progress in the optical function part because of ingredients contained in the adhesive when the adhesive cures, during packing and storage, and upon measurement. However, the surface-enhanced Raman scattering unit in accordance with one aspect of the present invention uses no adhesive and thus can inhibit the optical function part from deteriorating.

In the surface-enhanced Raman scattering unit in accordance with one aspect of the present invention, the holding part may have a pinching part pinching the surface-enhanced Raman scattering element in cooperation with the measurement board. This structure can securely hold the surface-enhanced Raman scattering element in the measurement board. This can also prevent conductor layers and the like formed on the substrate in the surface-enhanced Raman scattering element from peeling from the substrate.

In the surface-enhanced Raman scattering unit in accordance with one aspect of the present invention, the pinching part may be formed into a ring so as to surround the optical function part when seen in a thickness direction of the substrate, or a plurality of pinching parts may be arranged around the optical function part. These structures can stably hold the surface-enhanced Raman scattering element in the measurement board. When bringing the pinching part into contact with a predetermined part of a Raman spectroscopic analyzer in the case of performing Raman spectroscopic analysis, the pinching part can be utilized as a spacer for placing a focal point of excitation light at the optical function part. When the pinching part is formed into a ring so as to surround the optical function part, a region on the inside of the pinching part can be utilized as a cell (chamber) for a solution sample.

In the surface-enhanced Raman scattering unit in accordance with one aspect of the present invention, the measurement board may be provided with a depression containing at least a part of the surface-enhanced Raman scattering element on the substrate side and restraining the surface-enhanced Raman scattering element from moving in a direction perpendicular to the thickness direction of the substrate. This structure can position the surface-enhanced Raman scattering element with respect to the measurement board. This can also prevent the surface-enhanced Raman scattering element from shifting from the measurement board.

In the surface-enhanced Raman scattering unit in accordance with one aspect of the present invention, the holding part may be formed separately from the measurement board and mechanically secured to the measurement board. This structure can simplify the structure of the measurement board. In addition, as compared with the case where the holding part is secured to the measurement board with an adhesive, for example, the optical function part can be more inhibited from deteriorating because of ingredients contained in the adhesive.

In the surface-enhanced Raman scattering unit in accordance with one aspect of the present invention, the holding part may be formed integrally with the measurement board. This structure can reduce the number of components in the surface-enhanced Raman scattering unit. In addition, as compared with the case where the holding part is secured to the measurement board with an adhesive, for example, the optical function part can be more inhibited from deteriorating because of ingredients contained in the adhesive.

In the surface-enhanced Raman scattering unit in accordance with one aspect of the present invention, the measurement board may be formed integrally from a resin. This makes it harder for chipping to occur and thus can securely inhibit the optical function part from deteriorating because of chipped pieces adhering thereto.

In the surface-enhanced Raman scattering unit in accordance with one aspect of the present invention, the measurement board may be provided with a hollowed part so as to form a wall part extending in a direction perpendicular to a thickness direction of the measurement board. This structure prevents the measurement board from warping and thus can accurately place a focal point of excitation light at the optical function part when arranging the measurement board on a stage of a Raman spectroscopic analyzer in the case where Raman spectroscopic analysis is performed.

In the surface-enhanced Raman scattering unit in accordance with one aspect of the present invention, the holding part may pinch a side face of the surface-enhanced Raman scattering element.

A Raman spectroscopic analysis method in accordance with one aspect of the present invention comprises a first step of preparing the above-mentioned surface-enhanced Raman scattering unit and arranging a sample on the optical function part; and a second step, after the first step, of setting the surface-enhanced Raman scattering unit to a Raman spectroscopic analyzer, irradiating the sample arranged on the optical function part with excitation light, and detecting Raman-scattered light derived from the sample, so as to perform Raman spectroscopic analysis.

This Raman spectroscopic analysis method uses the above-mentioned surface-enhanced Raman scattering unit and thus can accurately perform Raman spectroscopic analysis.

Advantageous Effects of Invention

The present invention can provide a, surface-enhanced Raman scattering unit which can inhibit the optical function part from deteriorating and a Raman spectroscopic analysis method using such a surface-enhanced Raman scattering unit.

BRIEF DESCRIPTION OF DRAWINGS

FIG. 9 is a set of partly enlarged plan and sectional views of a modified example of the surface-enhanced Raman scattering unit of FIG. 1;

FIG. 13 is a partly enlarged sectional view of modified examples of the surface-enhanced Raman scattering unit of FIG. 10;

FIG. 15 is a set of partly enlarged plan and sectional views of a modified example of the surface-enhanced Raman scattering unit of FIG. 10;

FIG. 16 is a set of partly enlarged plan and sectional views of a modified example of the surface-enhanced Raman scattering unit of FIG. 10;

FIG. 18 is a partly enlarged sectional view of the surface-enhanced Raman scattering unit in accordance with a third embodiment of the present invention;

DESCRIPTION OF EMBODIMENTS

Figure 1:
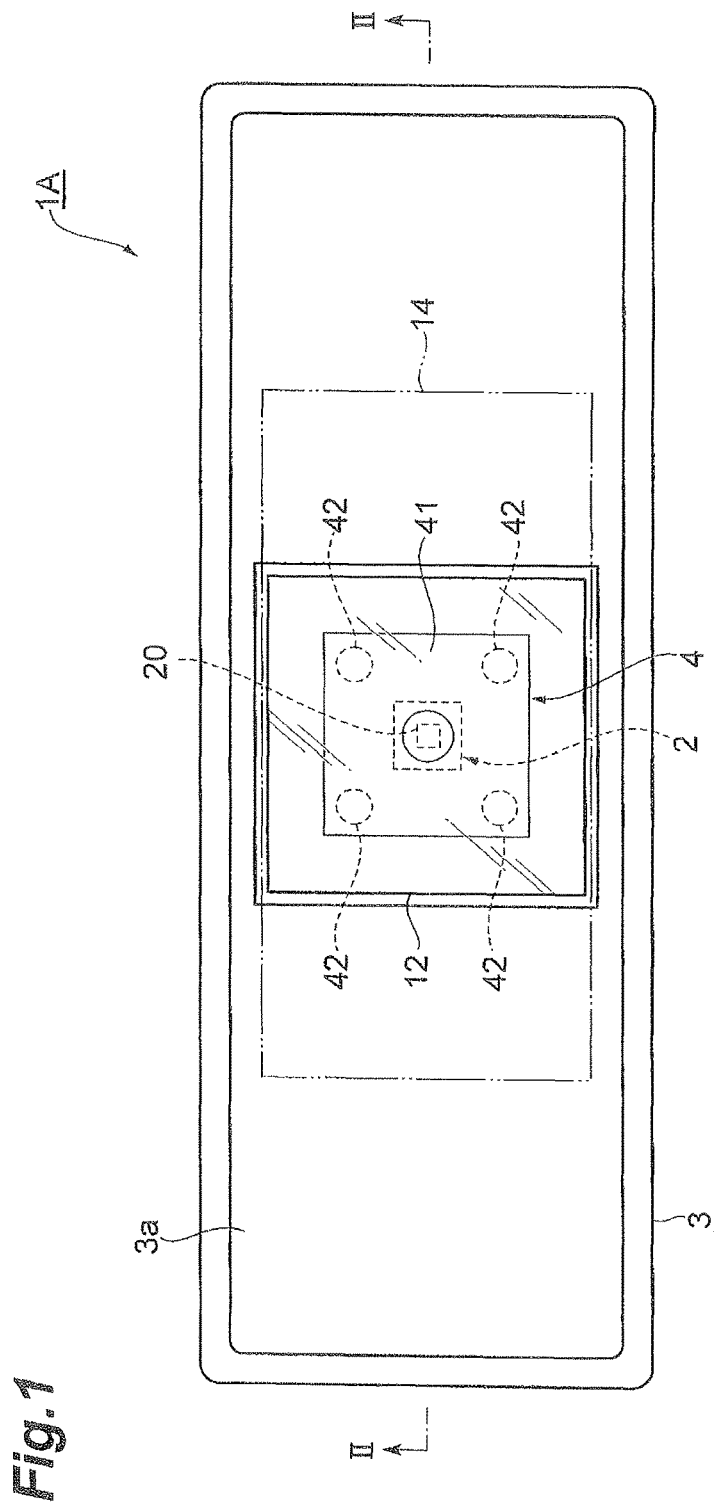
FIG. 1 is a plan view of the surface-enhanced Raman scattering unit in accordance with a first embodiment of the present invention.

In the following, preferred embodiments of the present invention will be explained in detail with reference to the drawings. In the drawings, the same or equivalent constituents will be referred to with the same signs while omitting their overlapping descriptions.

[First Embodiment]

Figure 2:
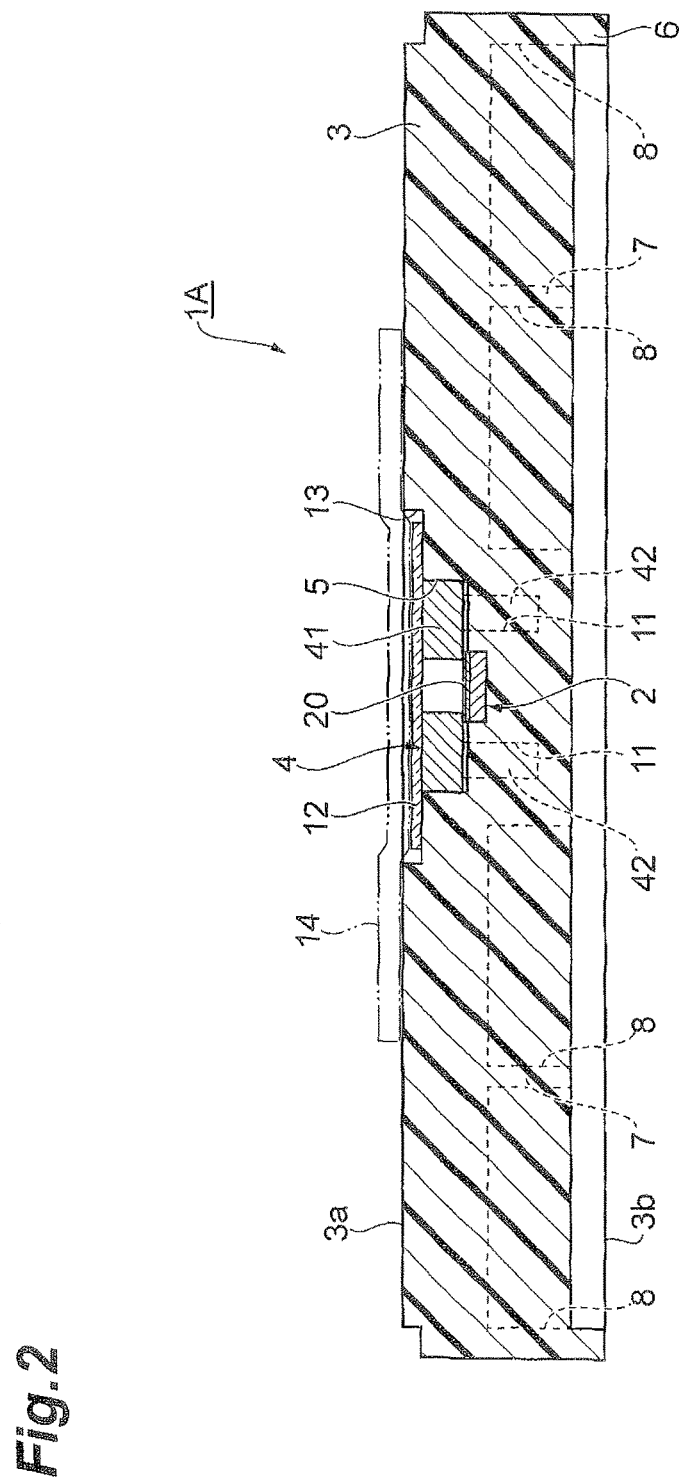
FIG. 2 is a sectional view of the surface-enhanced Raman scattering unit taken along the line II-II of FIG. 1.

As illustrated in FIGS. 1 and 2, a SERS unit (surface-enhanced Raman scattering unit) 1A comprises a SERS element (surface-enhanced Raman scattering element) 2, a measurement board 3 supporting the SERS element 2 upon measurement, and a holding member 4 mechanically holding the SERS element 2 in the measurement board 3. By "mechanically" is meant "through fitting between members without adhesives and the like."

Figure 3:
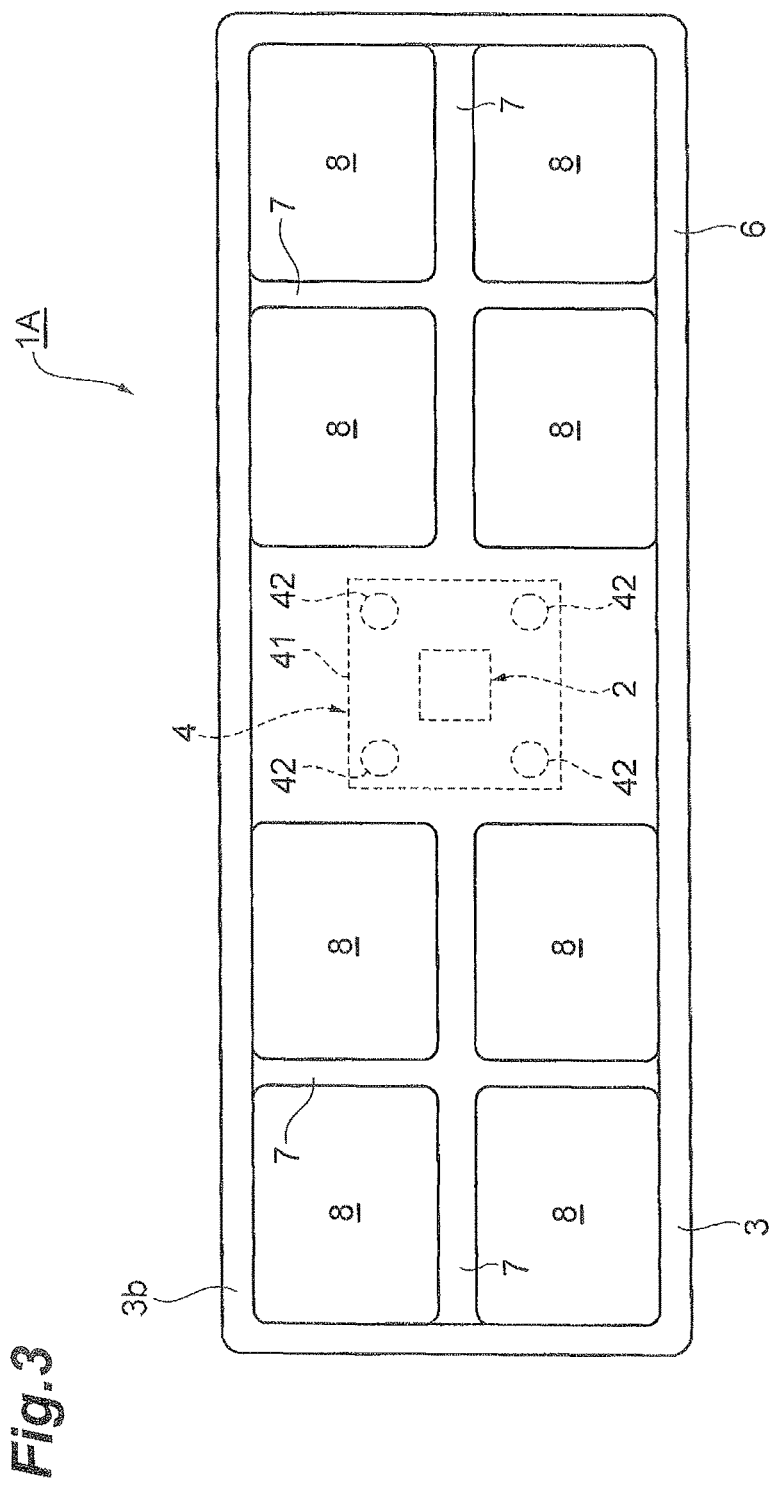
FIG. 3 is a bottom view of the surface-enhanced Raman scattering unit of FIG. 1.

The measurement board 3 has a front face 3a provided with a depression 5 containing the SERS element 2 and holding part 4. On the other hand, as illustrated in FIG. 3, the measurement board 3 has a rear face 3b provided with a plurality of hollowed parts 8 so as to form wall parts 6, 7 extending in directions perpendicular to the thickness direction of the measurement board 3. For example, the wall part 6 is formed like a ring along outer edges of the measurement board 3, while the wall part 7 is formed like grids on the inside of the wall part 6. For example, the measurement board 3 is formed into a rectangular plate. The depression 5 and hollowed parts 8 are formed into rectangular parallelepipeds. The measurement board 3 is integrally formed from materials such as resins (polypropylene, styrol resin, ABS resin, polyethylene, PET, PMMA, silicone, liquid crystal polymer, etc.), ceramics, glass, and silicon by using techniques such as molding, cutting, and etching.

Figure 4:
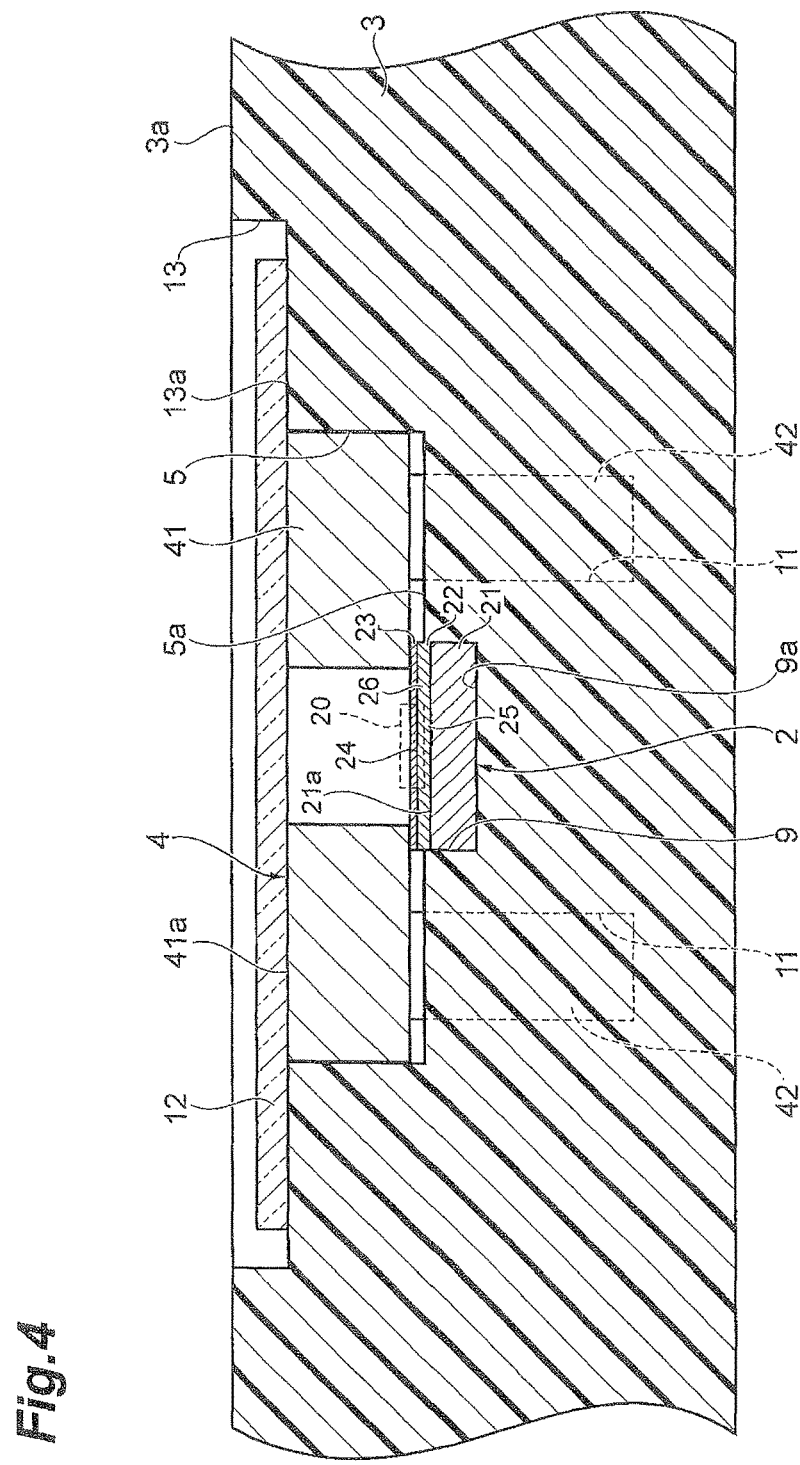
FIG. 4 is a partly enlarged sectional view of the surface-enhanced Raman scattering unit taken along the line II-II of FIG. 1.

As illustrated in FIG. 4, the SERS element 2 comprises a substrate 21, a molded layer 22 formed on the substrate 21, and a conductor layer 23 formed on the molded layer 22. For example, the substrate 21 is formed from silicon, glass, or the like into a rectangular plate having an outer form on the order of several hundred μm×several hundred μm to several ten mm×several ten mm and a thickness on the order of 100 μm to 2 mm.

The molded layer 22 has a fine structure part 24, a support part 25, and a frame part 26. The fine structure part 24, which is a region having a periodic pattern, is formed on a surface layer opposite from the substrate 21 at a center part of the molded layer 22. As the periodic pattern, a plurality of pillars each having a thickness and height on the order of several nm to several hundred nm are periodically arranged at a pitch on the order of several ten rim to several hundred nm in the fine structure part 24. The support part 25, which is a region supporting the fine structure part 24, is formed on a front face 21a of the substrate 21. The frame part 26, which is a ring-shaped region surrounding the support part 25, is formed on the front face 21a of the substrate 21.

For example, the fine structure part 24 has a rectangular outer form on the order of several hundred um x several hundred um to several mm x several ten mm when seen from one side in the thickness direction of the measurement board 3. The support part 25 and frame part 26 have a thickness on the order of several ten nm to several ten μm. The molded layer 22 is integrally formed by molding a resin (examples of which include resins based on acrylics, fluorine, epoxy, silicone, and urethane, PET, polycarbonate, and inorganic/organic hybrid materials) or low-melting glass arranged on the substrate 21 by nanoimprinting, for example.

The conductor layer 23 is formed over the fine structure part 24 to the frame part 26. In the fine structure part 24, the conductor layer 23 reaches a surface of the support part 25, exposed to the side opposite from the substrate 21. For example, the conductor layer 23 has a thickness on the order of several nm to several μm. The conductor layer 23 is formed by vapor-depositing a conductor such as a metal (Au, Ag, Al, Cu, Pt, or the like) on the molded layer 22 molded by nanoimprinting, for example.

Figure 5:
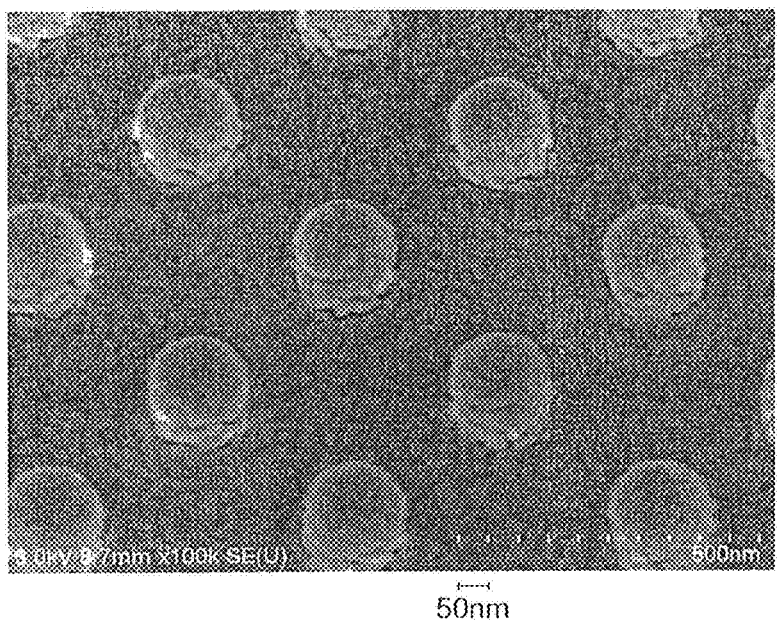
FIG. 5 is a SEM photograph of an optical function part in the surface-enhanced Raman scattering unit of FIG. 1.

In the SERS element 2, the conductor layer 23 formed over the surface of the fine structure part 24 and the surface of the support part 25 exposed to the side opposite from the substrate 21 produces an optical function part 20, which generates surface-enhanced Raman scattering, on the substrate 21. For reference, a SEM photograph of the optical function part 20 is illustrated. The optical function part illustrated in FIG. 5 is one in which Au is vapor-deposited as a conductor layer so as to have a thickness of 50 nm on a fine structure part made of a nanoimprint resin having a plurality of pillars (each having a diameter of 120 nm and a height of 180 nm) periodically arranged at a predetermined pitch (a distance of 360 nm between center lines).

As illustrated in FIG. 4, the depression 5 has a bottom face 5a provided with a depression 9 containing a part of the SERS element 2 on the substrate 21 side. The depression 9 is formed complementary to a part of the SERS element 2 on the substrate 21 side and restrains the SERS element 2 from moving in directions perpendicular to the thickness direction of the substrate 21. The SERS element 2 is not secured to the inner surface of the depression 9 with an adhesive or the like, but is only in contact with the inner surface of the depression 9.

The holding part 4 has a pinching part 41 formed into a ring so as to surround the optical function part 20 when seen in the thickness direction of the substrate 21 and a plurality of leg parts 42 extending from the pinching part 41 toward the rear face 3b of the measurement board 3. Fitting holes 11 are formed in the bottom face 5a of the depression 5 so as to correspond to the leg parts 42, respectively. The leg parts 42 are fitted into their corresponding fitting holes 11 in a state where the pinching part 41 surrounds the optical function part 20 and is in contact with the conductor layer 23 of the SERS element 2. Thus, the holding part 4 formed separately from the measurement board 3 is mechanically secured to the measurement board 3, while the SERS element 2 arranged in the depression 9 is pinched by the measurement board 3 and the pinching part 41 of the holding part 4. As a consequence, the SERS element 2 is mechanically held with respect to the measurement board 3. The fitting holes 11 do not penetrate through the measurement board 3 but are bottomed.

For example, the pinching part 41 is formed such as to have a rectangular outer edge and a circular inner edge when seen in the thickness direction of the substrate 21, while the leg parts 42 extend from four corners of the pinching part 41, respectively, toward the rear face 3b of the measurement board 3. Making the inner edge of the pinching part 41 circular prevents pressures from acting locally on the SERS element 2. The leg parts 42 and fitting holes 11 are formed cylindrical. The holding part 4 having the pinching part 41 and leg parts 42 is integrally formed from materials such as resins (polypropylene, styrol resin, ABS resin, polyethylene, PET, PMMA, silicone, liquid crystal polymer, etc.), ceramics, glass, and silicon by using techniques such as molding, cutting, and etching.

The SERS unit 1A further comprises a cover 12 which transmits light therethrough. The cover 12 is arranged at a widened part 13 provided in an opening part of the depression 5 and covers the opening part of the depression 5. The widened part 13 is formed complementary to the cover 12 and restrains the cover 12 from moving in directions perpendicular to the thickness direction of the cover 12. The pinching part 41 of the holding part 4 has a front face 41a substantially flush with a bottom face 13a of the widened part 13. As a consequence, the cover 12 is supported not only by the measurement board 3 but also by the holding part 4. For example, the cover 12 is formed from glass or the like into a rectangular plate having an outer form on the order of 18 mm×18 mm and a thickness on the order of 0.15 mm. Until the SERS unit 1A is used, a temporary securing film 14 is attached to the measurement board 3 so as to overlie the cover 12, whereby the cover 12 is prevented from dropping out of the measurement board 3.

Figure 6:
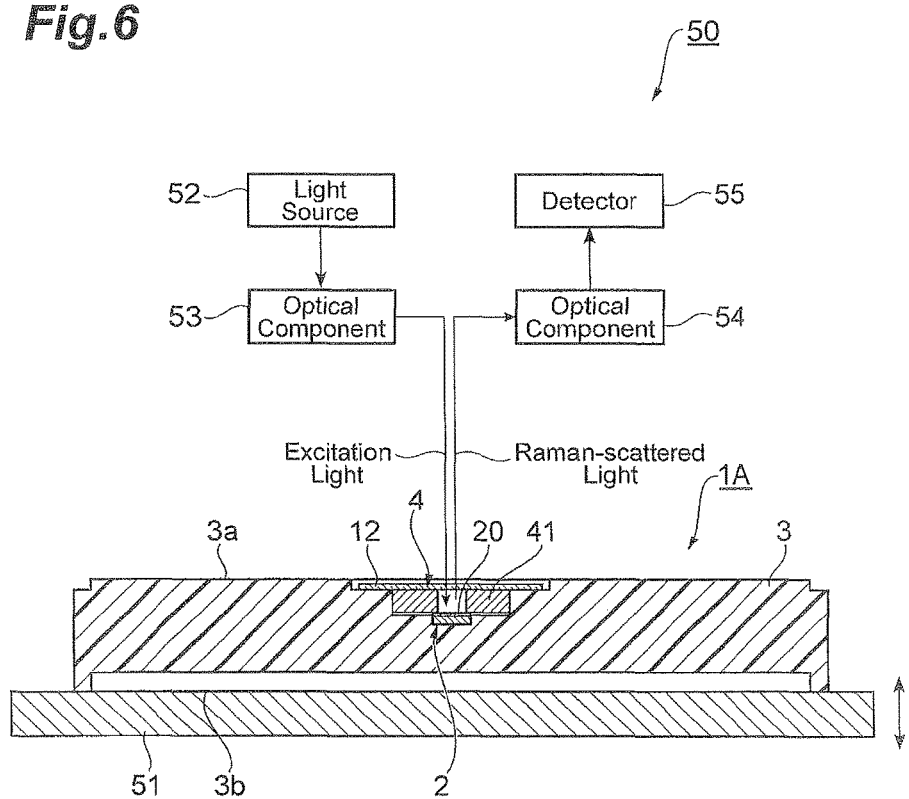
FIG. 6 is a structural diagram of a Raman spectroscopic analyzer to which the surface-enhanced Raman scattering unit of FIG. 1 is set.

A Raman spectroscopic analysis method using the SERS unit 1A will now be explained. Here, as illustrated in FIG. 6, the Raman spectroscopic analysis method is performed in a Raman spectroscopic analyzer 50 comprising a stage 51 supporting the SERS unit 1A, a light source 52 for emitting excitation light, an optical component 53 for effecting collimation, filtering, condensing, and the like necessary for irradiating the optical function part 20 with the excitation light, an optical component 54 for effecting collimation, filtering, and the like necessary for guiding Raman-scattered light to a. detector 55, and the detector 55 for detecting the Raman-scattered light.

First, the SERS unit 1A is prepared, the temporary securing film 14 is peeled off from the measurement board 3, and the cover 12 is removed from the measurement board 3. Then, a solution sample (or a dispersion of a powder sample in water or in a solution of ethanol) is dropped to a region on the inside of the pinching part 41 of the holding part 4, so as to be arranged on the optical function part 20 (first step). Subsequently, for reducing the lens effect, the cover 12 is arranged on the widened part 13 of the measurement board 3, so as to come into close contact with the solution sample.

Thereafter, the measurement board 3 is arranged on the stage 51, and the SERS unit 1A is set to the Raman spectroscopic analyzer 50. Subsequently, the solution sample arranged on the optical function part 20 is irradiated with the excitation light emitted through the optical component 53 from the light source 52. At this time, the stage 51 is moved such that a focal point of the excitation light is located at the optical function part 20. This causes surface-enhanced Raman scattering at the interface between the optical function part 20 and the solution sample, whereby Raman-scattered light derived from the solution sample is released after being enhanced by about $10^8$ times, for example. The released Raman-scattered light is detected by the detector 55 through the optical component 54, so as to perform Raman spectroscopic analysis (second step).

Not only the above-mentioned method but the following methods may also be used for arranging the sample on the optical function part 20. For example, the measurement board 3 may be held, so as to dip the SERS element 2 into a solution sample (or a dispersion of a powder sample in water or in a solution of ethanol or the like), lift it up, and then blow it to dry. A minute amount of a solution sample (or a dispersion of a powder sample in water or in a solution of ethanol or the like) may be dropped on the optical function part 20 and left to dry. A powder sample may be dispersed as it is on the optical function part 20.

Effects exhibited by the SERS unit 1A will now be explained. In the SERS unit 1A, the holding part 4 mechanically holds the SERS element 2 in the measurement board 3. Consequently, as compared with a case where the SERS element 2 is secured to the measurement board 3 with an adhesive, for example, the optical function part 20 is more inhibited from deteriorating because of ingredients contained in the adhesive. Therefore, the SERS unit 1A can restrain the optical function part 20 from deteriorating. As a result, the Raman spectroscopic analysis method using the SERS unit 1A can perform Raman analysis accurately.

In the SERS unit 1A, the holding part 4 has the pinching part 41 pinching the SERS element 2 in cooperation with the measurement board 3. This can securely hold the SERS element 2 in the measurement board 3. This can also prevent the molded layer 22 and conductor layer 23 formed on the substrate 21 in the SERS element 2 from peeling from the substrate 21.

In the SERS unit 1A, the pinching part 41 is formed into a ring so as to surround the optical function part 20 when seen in the thickness direction of the substrate 21. This can stably hold the SERS element 2 in the measurement board 3. Further, a region on the inside of the pinching part 41 can be utilized as a cell (chamber) for a solution sample. Even if the solution sample leaks out to a region on the outside of the pinching part 41, the bottomed fitting holes 11 provided in the bottom face 5a of the depression 5 in the measurement board 3 can prevent the solution sample from leaking out of the depression 5. When bringing the pinching part 41 into contact with a predetermined part of the Raman spectroscopic analyzer 50 in the case of performing Raman spectroscopic analysis (see FIG. 12), the pinching part 41 can be utilized as a spacer for placing a focal point of excitation light at the optical function part 20.

In the SERS unit 1A, the measurement board 3 is provided with the depression 9 containing a part of the SERS element 2 on the substrate 21 side and restraining the SERS element 2 from moving in directions perpendicular to the thickness direction of the substrate 21. This can position the SERS element 2 with respect to the measurement board 3. This can also prevent the SERS element 2 from shifting from the measurement board 3.

In the SERS unit 1A, the holding part 4 is formed separately from the measurement board 3 and mechanically secured to the measurement board 3. This can simplify the structure of the measurement board 3. In addition, as compared with a case where the holding part 4 is secured to the measurement board 3 with an adhesive, for example, the optical function part 20 can also be inhibited from deteriorating because of ingredients contained in the adhesive.

In the SERS unit 1A, the measurement board 3 is formed integrally from a resin. This makes it harder for chipping to occur and thus can securely inhibit the optical function part 20 from deteriorating because of chipped pieces adhering thereto. Further, embossing the outer surface of the measurement board 3 or using a resin having a light-absorbing color as a material for the measurement board 3 can inhibit stray light from occurring at the time of Raman spectroscopic analysis.

In the SERS unit 1A, the measurement board 3 is provided with a plurality of hollowed parts 8 so as to form the wall parts 6, 7 extending in directions perpendicular to the thickness direction of the measurement board 3. This prevents the measurement board 3 from warping and thus can accurately place a focal point of excitation light at the optical function part 20 when arranging the measurement board 3 on the stage 51 of the Raman spectroscopic analyzer 50 in the case where Raman spectroscopic analysis is performed.

Figure 7:
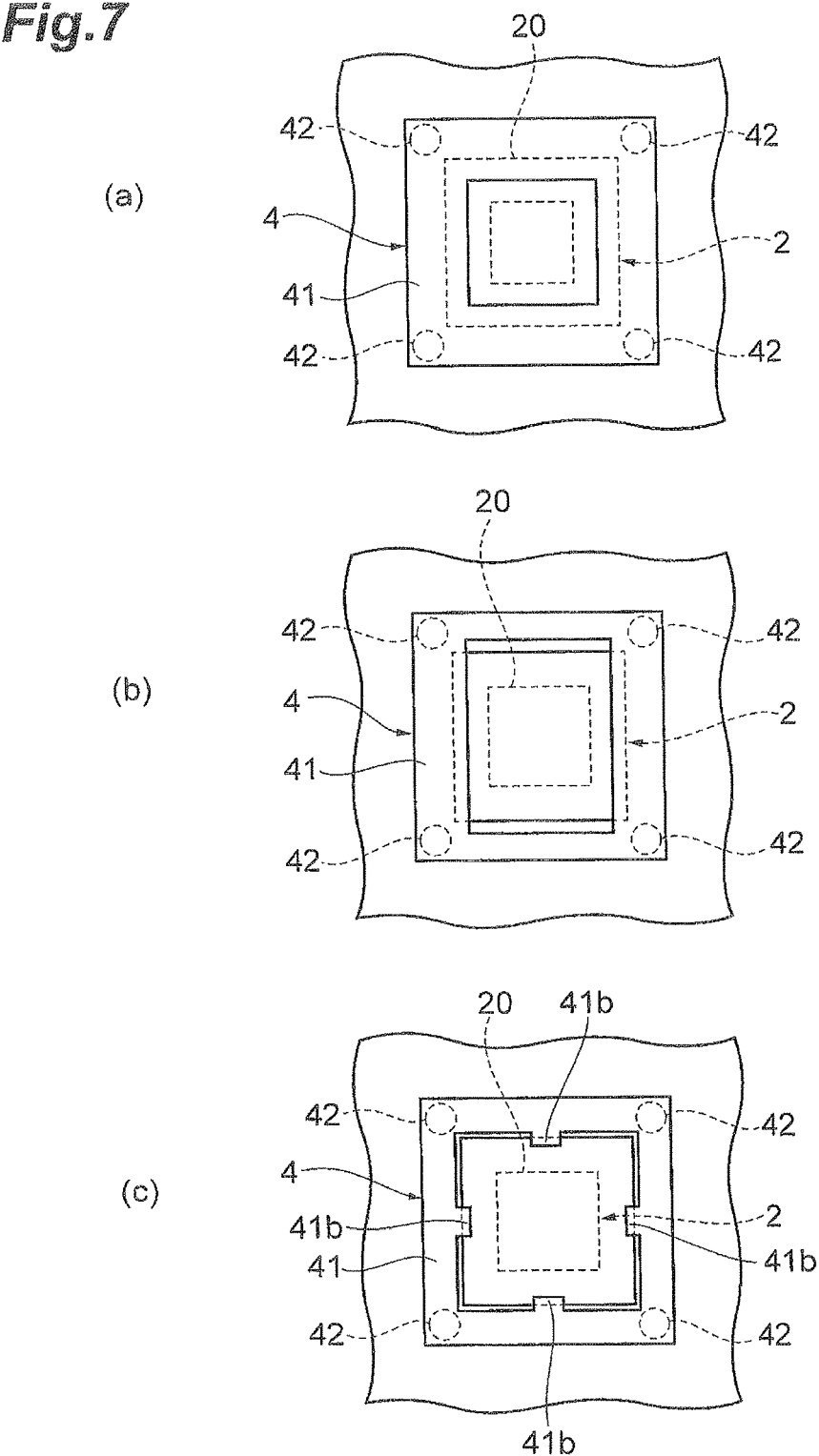
FIG. 7 is a partly enlarged plan view of modified examples of the surface-enhanced Raman scattering unit of FIG. 1.

Modified examples of the SERS unit 1A will now be explained. As illustrated in FIG. 7, the pinching part 41 of the holding part 4 may be formed so as to have a rectangular inner edge when seen in the thickness direction of the substrate 21. As illustrated in FIG. 7(a), the pinching part 41 may be formed such as to come into contact with the SERS element 2 in the ring-shaped region of its inner edge. As illustrated in FIG. 7(b), the pinching part 41 may be formed such as to come into contact with the SERS element 2 in areas opposing each other in the ring-shaped region of its inner edge. As illustrated in FIG. 7(c), the pinching part 41 may be formed such as to come into contact with the SERS element 2 at a plurality of projections 41b formed in its inner edge.

Figure 8:
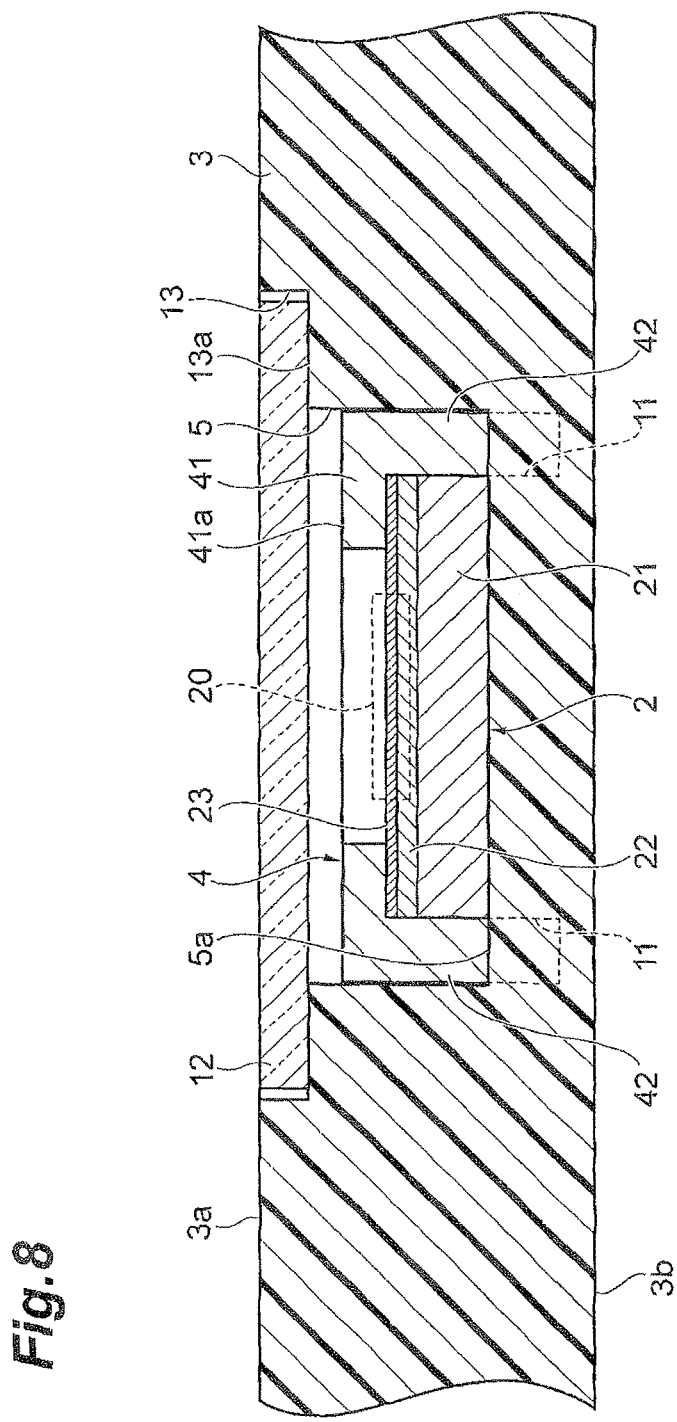
FIG. 8 is a partly enlarged sectional view of a modified example of the surface-enhanced Raman scattering unit of FIG. 1.

As illustrated in FIG. 8, the front face 41a of the pinching part 41 of the holding part 4 may be located on the inside of the depression 5 with respect to the bottom face 13a of the widened part 13 of the measurement board 3. In this case, the cover 12 is supported by the measurement board 3 alone. As illustrated in FIG. 9, one of parts opposing each other in the ring-shaped pinching part 41 may be rotatably supported by the measurement board 3, while the other is adapted to engage the measurement board 3. This structure makes it possible to manage the measurement board 3 and holding part 4 in a state where the holding part 4 is attached to the measurement board 3. When assembling the SERS unit 1A, the holding part 4 can easily hold the SERS element 2 by arranging the SERS element 2 in the depression 9 while the holding part 4 is open and then closing the holding part 4 so as to engage the other part of the pinching part 41 with the measurement board 3. For making it easier to open and close the holding part 4, a spring may be installed between the one part of the holding part 4 and the measurement board 3.

[Second Embodiment]

Figure 10:
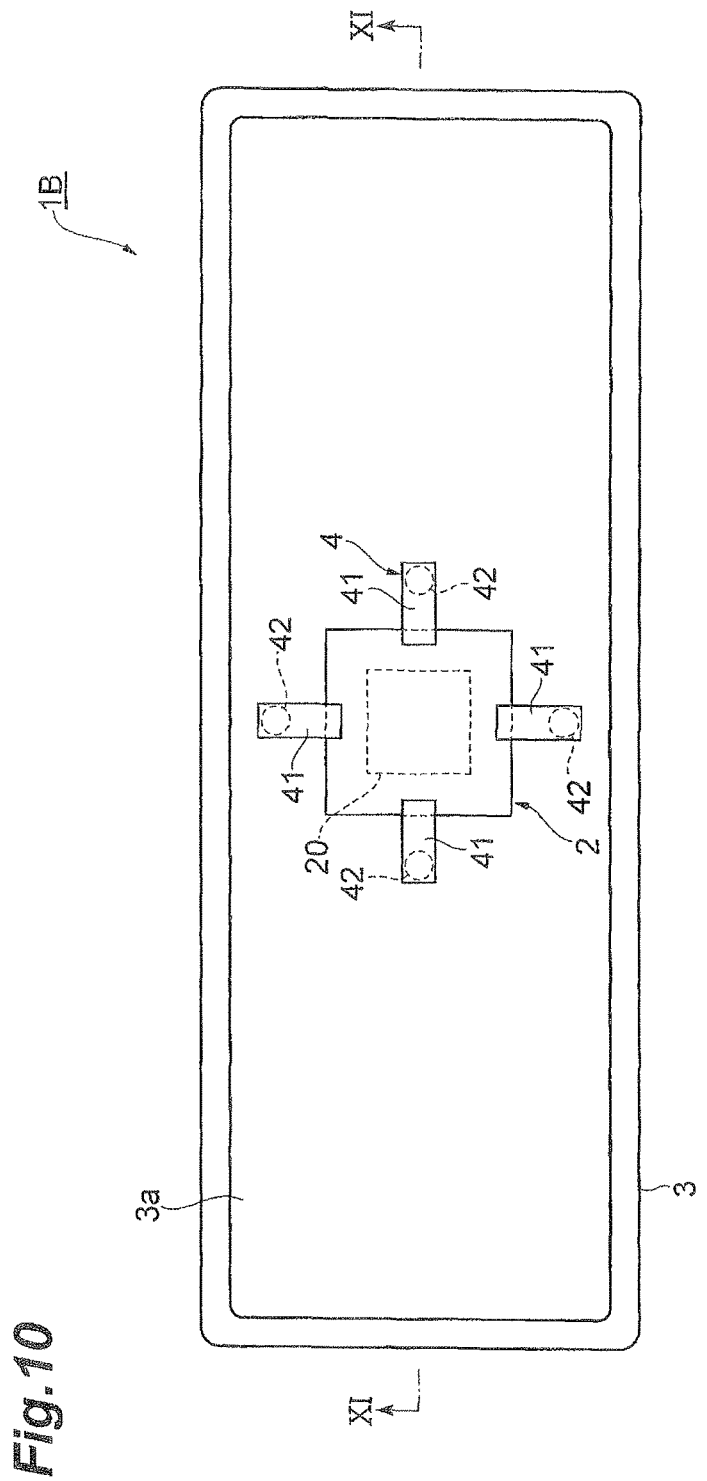
FIG. 10 is a plan view of the surface-enhanced Raman scattering unit in accordance with a second embodiment of the present invention.
Figure 11:
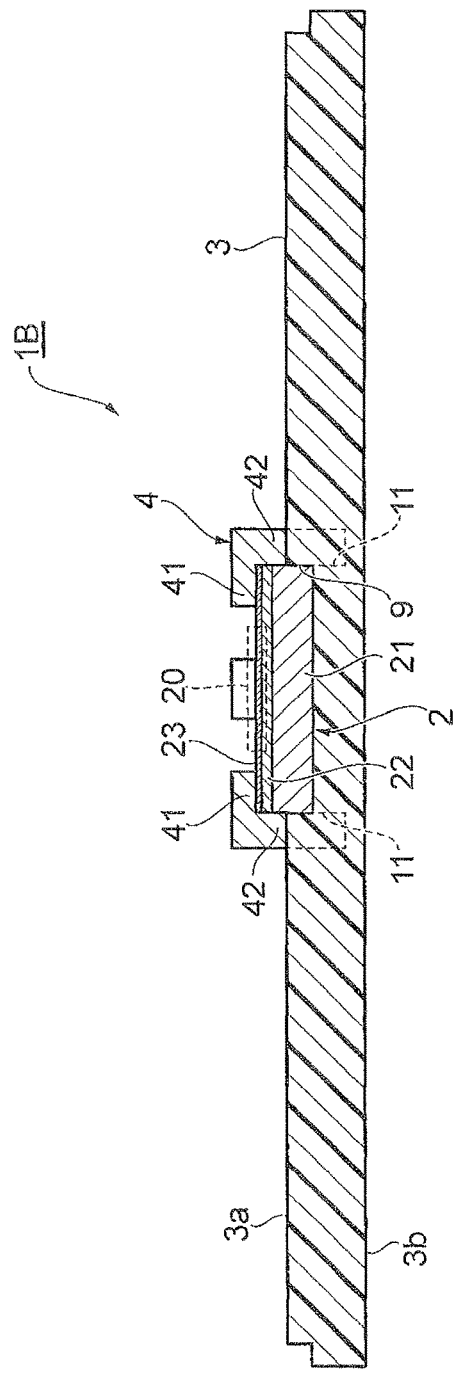
FIG. 11 is a sectional view of the surface-enhanced Raman scattering unit taken along the line XI-XI of FIG. 10.

As illustrated in FIGS. 10 and 11, a SERS unit 1B differs from the above-mentioned SERS unit 1A mainly in that a plurality of pinching parts 41 of the holding part 4 are arranged around the optical function part 20 of the SERS element 2. In the SERS unit 1B, the depression 9 containing a part of the SERS element 2 on the substrate 21 side is provided in the front face 3a of the measurement board 3. The holding part 4 has a plurality of pinching parts 41 arranged around the optical function part 20 of the SERS element 2 and leg parts 42 extending from the respective pinching parts 41 toward the rear face 3b of the measurement board 3. Fitting holes 11 are provided in the front face 3a of the measurement board 3 so as to correspond to the respective leg parts 42. The leg parts 42 are fitted into the respective fitting holes 11 in a state where the pinching parts 41 are in contact with the conductor layer 23 of the SERS element 2.

In the SERS unit 1B, the holding part 4 holds the SERS element 2 mechanically in the measurement board 3 as in the above-mentioned SERS unit 1A. Therefore, the SERS unit 1B can inhibit the optical function part 20 from deteriorating.

In the SERS unit 1B, the holding part 4 has the pinching part 41 pinching the SERS element 2 in cooperation with the measurement board 3 as in the above-mentioned SERS unit 1A. This can securely hold the SERS element 2 in the measurement board 3. This can also prevent the molded layer 22 and conductor layer 23 formed on the substrate 21 in the SERS element 2 from peeling from the substrate 21.

Figure 12:
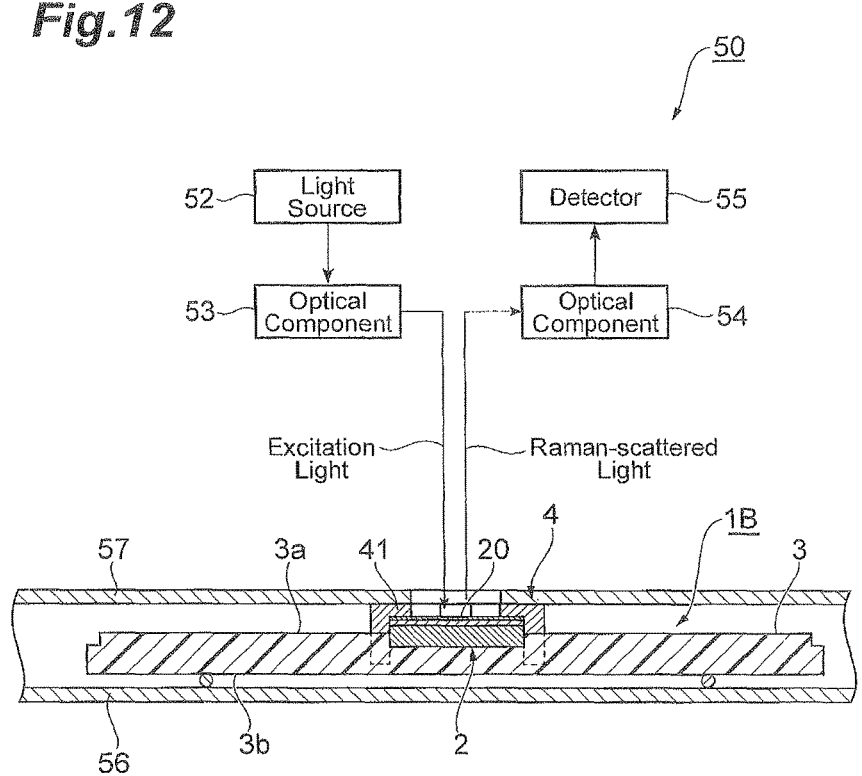
FIG. 12 is a structural diagram of a Raman spectroscopic analyzer to which the surface-enhanced Raman scattering unit of FIG. 10 is set.

In the SERS unit 1B, a plurality of holding parts 41 are arranged around the optical function part 20. This makes it possible to hold the SERS element 2 stably in the measurement board 3. Further, as illustrated in FIG. 12, when setting the SERS unit 1B to a pressing mechanism 56 of the Raman spectroscopic analyzer 50 so as to bring the pinching parts 41 into contact with a holder 57 of the Raman spectroscopic analyzer 50 in the case of performing Raman spectroscopic analysis, the pinching parts 41 can be utilized as spacers for placing a focal point of excitation light at the optical function part 20. At this time, the contact parts 41 also prevent the optical function part 20 from being damaged by physical contact.

In the SERS unit 1B, the pinching parts 41 are rotatable around their corresponding leg parts 42 with respect to the measurement board 3. As a consequence, at a stage prior to assembling the SERS unit 1B, the measurement board 3 and holing part 4 can be managed in a state where the holding part 4 is attached to the measurement board 3 while the pinching parts 41 are retracted from above the depression 9 of the measurement board 3. When assembling the SERS unit 1B, arranging the SERS element 2 in the depression 9 and then rotating the pinching parts 41 around the leg parts 42 enables the holding part 4 to hold the SERS element 2 easily.

Modified examples of the SERS unit 1B will now be explained. As illustrated in FIG. 13(a), guide grooves 15 for arranging the respective leg parts 42 of the holding part 4 may be provided in side faces of the depression 9 formed in the measurement board 3. This structure enables the leg parts 42 to fit into the fitting holes 11 easily and securely. In this case, the leg parts 42 can also position the SERS element 2. As illustrated in FIG. 13(b), the depression 9 can also position the SERS element 2 in the case where the guide grooves 15 are provided.

Figure 14:
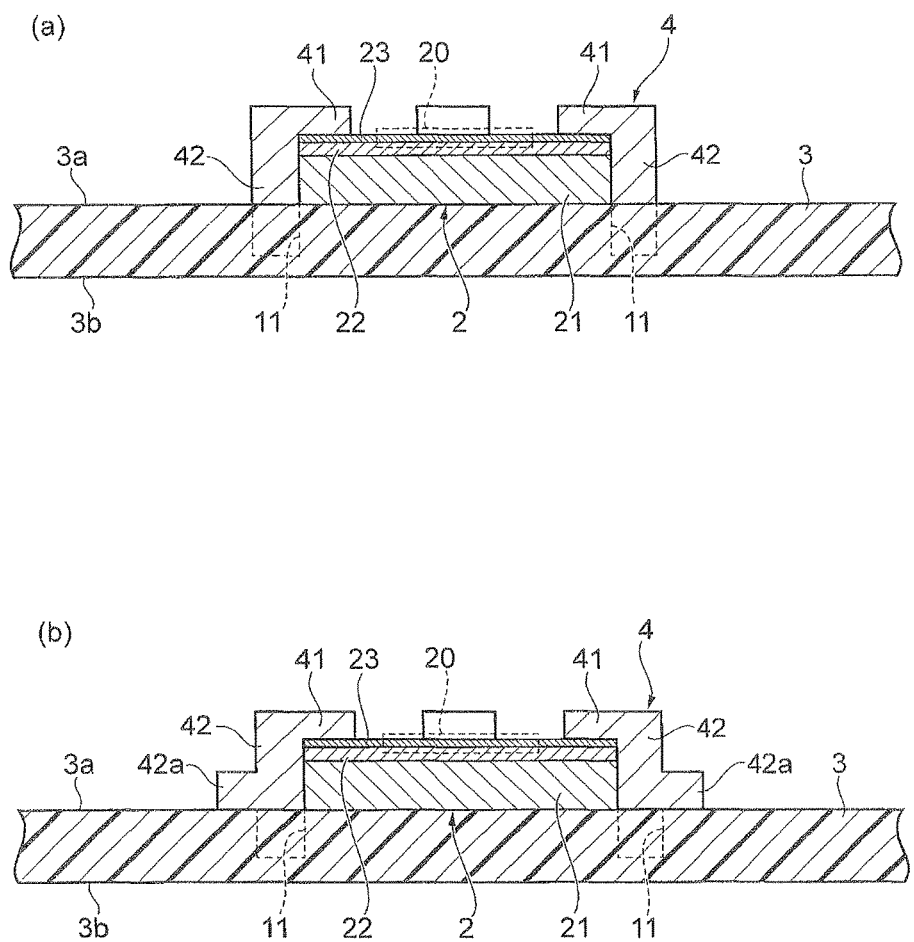
FIG. 14 is a partly enlarged sectional view of modified examples of the surface-enhanced Raman scattering unit of FIG. 10.

As illustrated in FIG. 14(a), the SERS element 2 may be arranged in the front face 3a of the measurement board 3. That is, the lower face of the substrate 21 of the SERS element 2 may abut against the front face 3a of the measurement board 3. This structure can improve the strength of the measurement board 3 by the absence of the depression 9. As illustrated in FIG. 14(b), the leg parts 42 of the holding part 4 may be formed with stoppers 42a, respectively. In this structure, fitting the leg parts 42 into the fitting holes 11 until the stoppers 42a come into contact with the measurement board 3 enables the pinching parts 41 to come into contact with the SERS element 2 and exert a substantially fixed pressure thereon, thereby preventing the pressure from acting more than necessary on the SERS element 2.

As illustrated in FIG. 15, for restricting rotation areas of the pinching parts 41 when the pinching parts 41 are rotated around the leg parts 42 with respect to the measurement board 3, the front face 3a of the measurement board 3 may be provided with depressions 16. At a stage prior to assembling the SERS unit 1B, this structure enables the pinching parts 41 to be retracted from above the depression 9 of the measurement board 3 to substantially fixed positions. Therefore, when assembling the SERS unit 1B, an operation of rotating the pinching parts 41 around the leg parts 42 so as to make the holding part 4 hold the SERS element 2 can be done efficiently.

Figure 17:
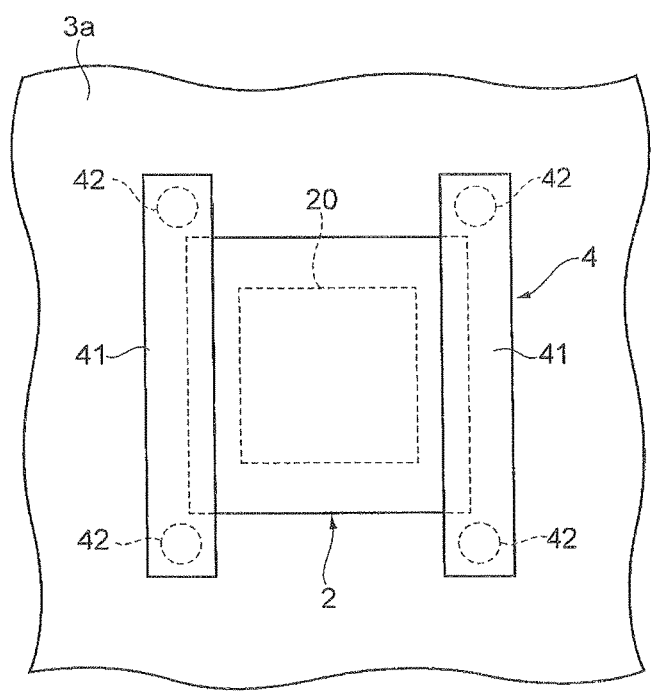
FIG. 17 is a partly enlarged plan view of a modified example of the surface-enhanced Raman scattering unit of FIG. 10.

As illustrated in FIG. 16, the holding part 4 may engage the measurement board 3 such that the holding parts 41 can advance and retract with respect to the SERS element 2 arranged in the depression 9. As illustrated in FIG. 17, a plurality of pinching parts 41 may be arranged such as to come into contact with the SERS element 2 in each of areas opposing each other in the ring-shaped region in the outer edge of the SERS element 2.

[Third Embodiment]

As illustrated in FIG. 18, a SERS unit 1C differs from the above-mentioned. SERS unit 1B mainly in that the holding part 4 is formed integrally with the measurement board 3. When assembling the SERS unit 1C, the holding part 4 is deformed such as to open each pinching part 41 as illustrated in FIG. 18(a), so that the SERS element 2 is arranged on the measurement board 3, and then the deformed holding part 4 is returned to its original state so as to close each pinching part 41 as illustrated in FIG. 18(b), thereby causing the holding part 4 to hold the SERS element 2.

In the SERS unit 1C constructed as in the foregoing, the holding part 4 mechanically holds the SERS element 2 in the measurement board 3 as in the above-mentioned SERS unit 1B. Therefore, the SERS unit 1C can inhibit the optical function part 20 from deteriorating.

In the SERS unit 1C, the holding part 4 has the pinching part 41 pinching the SERS element 2 in cooperation with the measurement board 3 as in the above-mentioned SERS unit 1B. This can hold the SERS element 2 securely in the measurement board 3. This can also prevent the molded layer 22 and conductor layer 23 formed on the substrate 21 in the SERS element 2 from peeling from the substrate 21.

In the SERS unit 1C, the holding part 4 is formed integrally with the measurement board 3. This can reduce the number of components in the surface-enhanced Raman scattering unit 1C. In addition, as compared with the case where the holding part 4 is secured to the measurement board 3 with an adhesive, for example, the optical function part 20 can be more inhibited from deteriorating because of ingredients contained in the adhesive.

Figure 19:
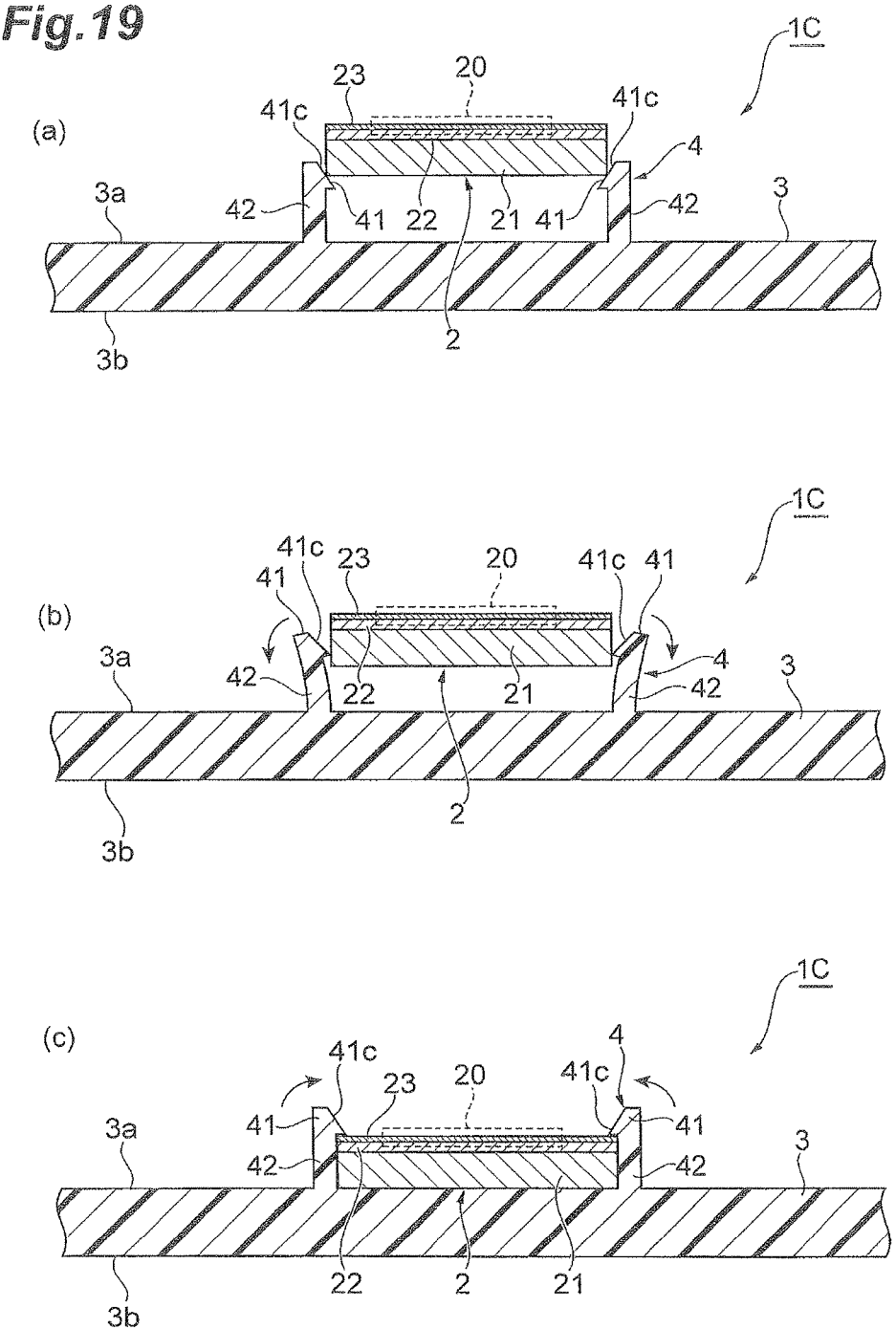
FIG. 19 is a partly enlarged sectional view of a modified example of the surface-enhanced Raman scattering unit of FIG. 18.
Figure 20:
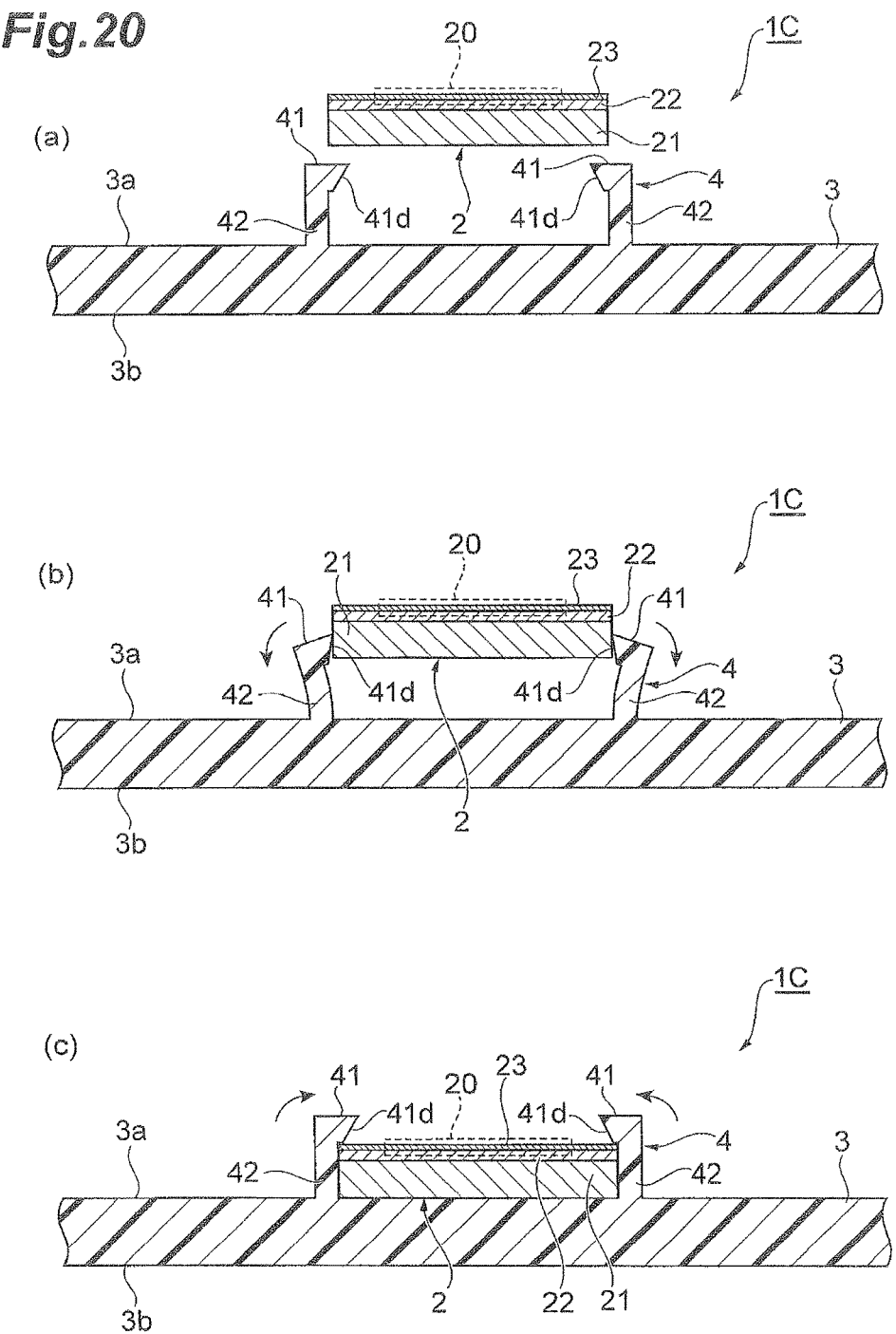
FIG. 20 is a partly enlarged sectional view of a modified example of the surface-enhanced Raman scattering unit of FIG. 18.
Figure 21:
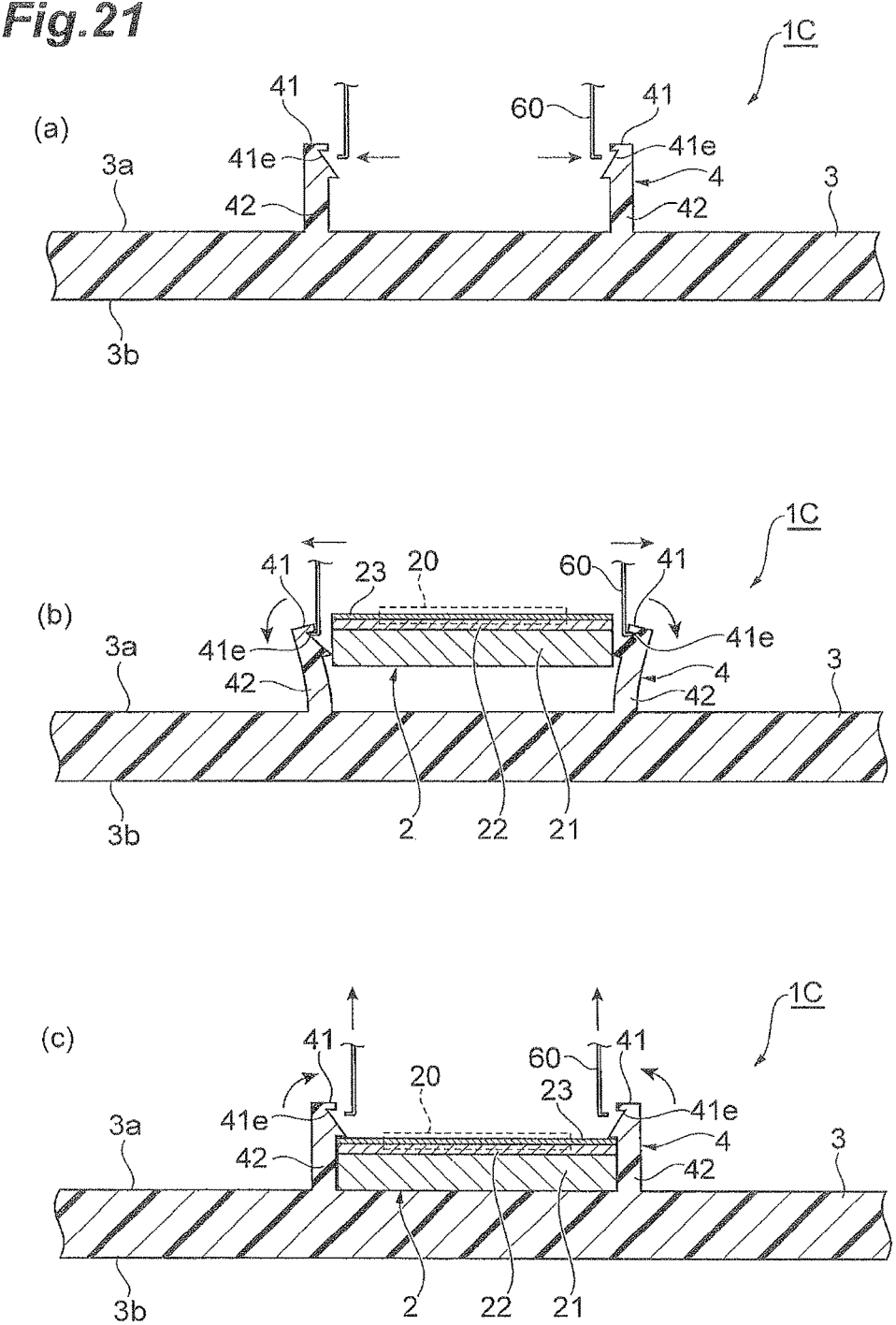
FIG. 21 is a partly enlarged sectional view of a modified example of the surface-enhanced Raman scattering unit of FIG. 18.

Modified examples of the SERS unit 1C will now be explained. As illustrated in FIG. 19, each pinching part 41 may have a tilted surface 41c formed so as to widen toward the side opposite from the measurement board 3. This structure can easily guide the SERS element 2 to its holding position in the measurement board 3 when assembling the SERS unit 1C. This can also inhibit stray light from occurring at the time of Raman spectroscopic analysis. As illustrated in FIG. 20, each pinching part 41 may have a tilted surface 41d formed so as to widen toward the measurement board 3. This structure can facilitate an operation of deforming the holding part 4 so as to open each pinching part 41 when assembling the SERS unit 1C. As illustrated in FIG. 21, each pinching part 41 may have a cutout 41e for engaging a jig 60 used for the operation of deforming the holding part 4 so as to open each pinching part 41. This structure can facilitate the operation of deforming the holding part 4 so as to open each pinching part 41 by using the jig 60, while securely preventing the jig 60 from coming into contact with the optical function part 20 when assembling the SERS unit 1C.

Figure 22:
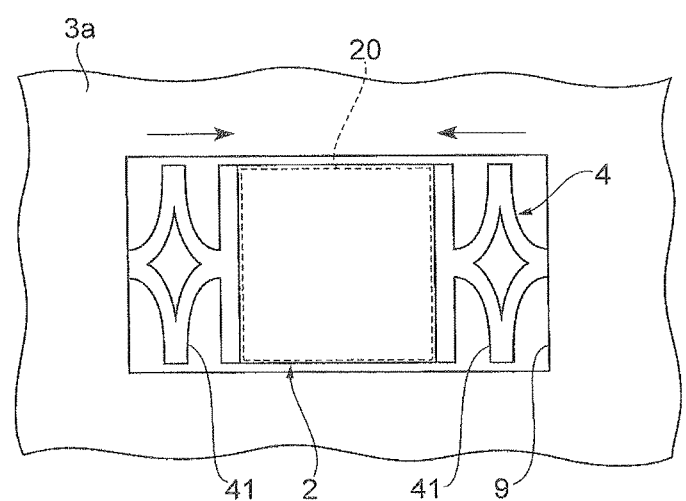
FIG. 22 is a partly enlarged plan view of the surface-enhanced Raman scattering unit in accordance with another embodiment of the present invention.

While the first to third embodiments of the present invention are explained in the foregoing, the present invention is not limited to the above-mentioned embodiments. For example, as illustrated in FIG. 22, a spring-shaped holding part 4 pinching the SERS element 2 in a direction parallel to the front face 3a of the measurement board 3 may be formed integrally with the measurement board 3 within the depression 9 for arranging the SERS element 2. This structure enables substantially the whole area of the front face of the SERS element 2 to serve as the optical function part 20.

Figure 23:
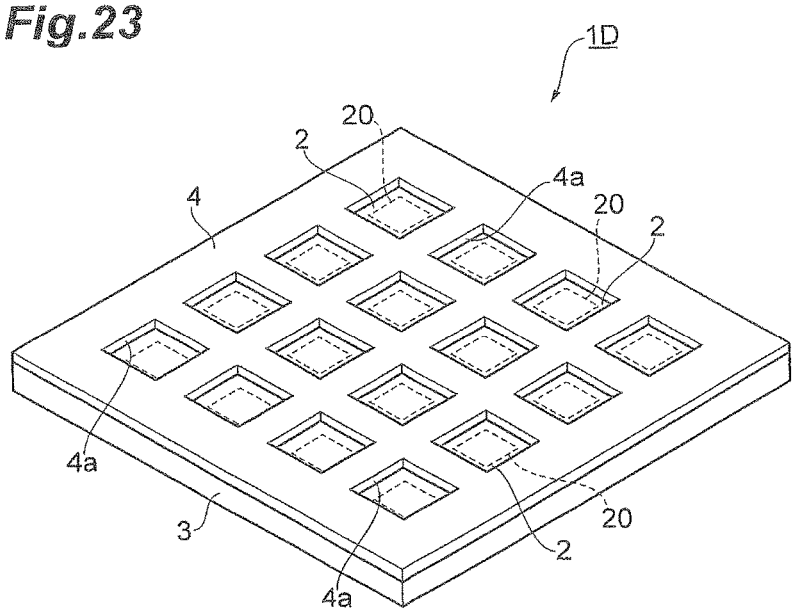
FIG. 23 is a perspective view of the surface-enhanced Raman scattering unit in accordance with still another embodiment of the present invention.

As illustrated in FIG. 23, a plurality of SERS elements 2 may be arranged on the measurement board 3, while a holding part 4 having a plurality of openings 4a corresponding to the respective optical function parts 20 of the SERS element 2 is attached to the measurement board 3. Thus constructed SERS unit 1D can efficiently perform Raman spectroscopic analysis for a plurality of samples.

The material for the measurement board 3 is not limited to resins, but may be low-melting glass, ceramics, and the like. The measurement board 3 can be formed integrally from low-melting glass as from a resin. From a ceramic, the measurement board 3 can be formed by firing, for example. Not only the above-mentioned materials and forms, but various materials and forms can also be employed for the structures of the SERS units 1A to 1D. The ring shape is not limited to circular rings, but encompasses other ring shapes such as rectangular rings.

The fine structure part 24 may be formed on the front face 21a of the substrate 21 either indirectly with the support part 25, for example, interposed therebetween or directly. The conductor layer 23 is not limited to the one directly formed on the fine structure part 24, but may indirectly be formed on the fine structure part 24 through some layers such as buffer metal (Ti, Cr, and the like) layers for improving the adhesion of the metal to the fine structure part 24.

INDUSTRIAL APPLICABILITY

The present invention can provide a surface-enhanced Raman scattering unit which can inhibit the optical function part from deteriorating and a Raman spectroscopic analysis method using such a surface-enhanced Raman scattering unit.

REFERENCE SIGNS LIST 1A, 1B, 1C, 1D: SERS unit (surface-enhanced Raman scattering unit); 2: SERS element (surface-enhanced Raman scattering element); 3: measurement board; 4: holding part; 6, 7: wall part; 8: hollowed part; 9: depression; 20: optical function part; 21: substrate; 41: pinching part.

The invention claimed is:

1. A surface-enhanced Raman scattering unit comprising:
a surface-enhanced Raman scattering element having a substrate and an optical function part formed on the substrate, the optical function part for generating surface-enhanced Raman scattering;
a measurement board supporting the surface-enhanced Raman scattering element upon measurement; and
a holding part mechanically holding the surface-enhanced Raman scattering element in the measurement board,
wherein the holding part is in contact with the surface-enhanced Raman scattering element, and
wherein the holding part does not overlap with at least part of the optical function part when viewed from the thickness direction of the substrate.

2. A surface-enhanced Raman scattering unit according to claim 1, wherein the holding part has a pinching part pinching the surface-enhanced Raman scattering element in cooperation with the measurement board.

3. A surface-enhanced Raman scattering unit according to claim 2, wherein a plurality of such pinching parts are arranged around the optical function part.

4. A surface-enhanced Raman scattering unit according to claim 1, wherein the measurement board is provided with a depression containing at least a part of the surface-enhanced Raman scattering element on the substrate side and restraining the surface-enhanced Raman scattering element from moving in a direction perpendicular to a thickness direction of the substrate.

5. A surface-enhanced Raman scattering unit according to claim 1, wherein the holding part is formed separately from the measurement board and mechanically secured to the measurement board.

6. A surface-enhanced Raman scattering unit according to claim 1, wherein the holding part is formed integrally with the measurement board.

7. A surface-enhanced Raman scattering unit according to claim 1, wherein the measurement board is formed integrally from a resin.

8. A surface-enhanced Raman scattering unit according to claim 7, wherein the measurement board is provided with a hollowed part so as to form a wall part extending in a direction perpendicular to a thickness direction of the measurement board.

9. A surface-enhanced Raman scattering unit according to claim 1, wherein the holding part pinches a side face of the surface-enhanced Raman scattering element.

10. A Raman spectroscopic analysis method comprising:
a first step of preparing the surface-enhanced Raman scattering unit according to claim 1 and arranging a sample on the optical function part; and
a second step, after the first step, of setting the surface-enhanced Raman scattering unit to a Raman spectroscopic analyzer, irradiating the sample arranged on the optical function part with excitation light, and detecting Raman-scattered light derived from the sample, so as to perform Raman spectroscopic analysis.

* * * * *